US00PP08665P

United States Patent [19]

VandenBerg

[11] Patent Number: Plant 8,665

[45] Date of Patent: Mar. 29, 1994

[54] CHRYSANTHEMUM PLANT NAMED YELLOW TAYRONA

[75] Inventor: Cornelis P. VandenBerg, Salinas, Calif.

[73] Assignee: Yoder Brothers, Inc., Barberton, Ohio

[21] Appl. No.: 919,257

[22] Filed: Jul. 27, 1992

[51] Int. Cl.[5] ..... A01H 5/00

[52] U.S. Cl. ..... Plt./78

[58] Field of Search ..... Plt. 76, 78, 77

[56] References Cited

U.S. PATENT DOCUMENTS

| | | | |
|---|---|---|---|
| PLT7673 | 10/1991 | VandenBerg | Plt 82.2 |
| PLT7600 | 7/1991 | VandenBerg | Plt 82.2 |
| PLT7511 | 4/1991 | VandenBerg | Plt 82.2 |
| PLT6954 | 7/1989 | VandenBerg | Plt 82.2 |
| PLT6943 | 7/1989 | VandenBerg | Plt 82.2 |
| PLT6881 | 6/1989 | VandenBerg | Plt 82.1 |
| PLT6399 | 11/1988 | Duffett et al. | Plt 82.1 |
| 4,616,099 | 10/1986 | Sparkes | 47/58 |

OTHER PUBLICATIONS

Broertjes, et al., 1980, "A mutant of a mutant of a . . . Irradiation of progressive radiation-induced mutants in a mutation breeding programme with *C. morifolium*", Euphytica, 29:526–530.

Gosling, ed., 1979, "The Chrysanthemum Manual-6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle, et al., 1968, "Chrysanthemums the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation Breeding of Chrysanthemums", Euphytica, 15:156–162.

Dowrick, et al., 1966, "the induction of mutations in Chrysanthemum using X-and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Yellow Tayrona particularly characterized by its flat capitulum form; decorative capitulum type; yellow ray floret color, with a fresh green center of the flower; diameter across face of capitulum of 63 to 73 mm when fully opened, when grown as a single stem spray cut mum; photoperiodic flowering response to short days when grown in Salinas, Calif., is 50 to 59 days after start of short days; flowering response in Bogota, Colombia, under temperatures of minimum 7 degrees Celsius night and maximum 29 degrees Celsius day is 63 to 67 days; plant height is 74 to 79 cm when grown in Salinas with 7 to 10 long days prior to start of short days; height is 99 to 124 cm when grown in Bogota with 14 long days prior to start of short days; peduncle length of the first lateral at flowering after removing the apical bud without growth regulator applications is 10 to 13 cm when grown in Salinas, and 13 to 18 cm when grown in Bogota; peduncle length of the fourth lateral at flowering is 13 to 15 cm when grown in Salinas, and 18 to 23 cm when grown in Bogota; and excellent tolerance to low night temperatures for bud initiation and flower development.

1 Drawing Sheet

The present invention comprises a new and distinct cultivar of Chrysanthemum, botanically known as *Dendranthema grandiflora,* and referred to by the cultivar name Yellow Tayrona.

Yellow Tayrona, identified as 0584 (85-249A04), is a product of a mutation induction program. The new cultivar was discovered and selected by Cornelis P. VandenBerg on Nov. 13, 1989 in a controlled environment in Salinas, Calif., as one flowering plant within a flowering block established as rooted cuttings from stock plants which had been exposed as unrooted cuttings to an X-ray source of 2000 rads in Fort Myers, Fla., on May 11, 1989. The irradiated parent cultivar was the cultivar identified as Tayrona, disclosed in U.S. Plant Pat. No. 7,482. Tayrona is described as a decorative spray cut mum with a flat capitulum form; a white ray floret color with a fresh green center of the flower; diameter across face of capitulum of 63 to 73 mm when fully opened; flowering response period of 50 to 57 days after start of short days in Salinas, Calif., and of 64 to 68 days in Bogota, Colombia; plant height of 74 to 86 cm when grown in Salinas with 6 to 11 long days prior to start of short days, and of 97 to 119 cm when grown in Bogota with 14 to 15 long days prior to start of short days; and excellent tolerance to low night temperatures for bud initiation and flower development. The above description of Tayrona has a wider range of measurements than the description of Tayrona in U.S. Plant Pat. No. 7,482. This is based on the continued flowering trials of Tayrona after preparing the plant patent application for Tayrona. Tayrona was commercially introduced in July 1990.

The irradiation program resulting in Yellow Tayrona had as its primary objective the expansion of color ranges of the parent cultivar Tayrona. The irradiation program comprised irradiating cuttings of the parent cultivar at irradiation levels of 1500, 1750 and 2000 rads. A total of 1198 cuttings harvested from a total of 225 irradiated plants were planted on Sep. 11, 1989, Sep. 4, 1989 and Aug. 21, 1989 for plants irradiated at 1500 rads, 1750 rads and 2000 rads, respectively. Of these, 16 initial selections were made, which selections were then revegetated and reflowered. Four consecutive flowerings resulted in discarding 12 of the original 16 selections on Sept. 4, 1990. Three codes (plants) were reselected prior to discarding on the same date, while four codes were retained as PI (Possible Introduction) status. The four retained codes and the three reselections were tested in Salinas, Calif., and in Bogota, Colombia, ultimately resulting in discarding five of these codes, and the decision to introduce one code 0584 as Yellow Tayrona and one reselected code 0804 as Lemon Tayrona, the latter being disclosed in pending application Ser. No. 07/919760.

The first act of asexual reproduction of Yellow Tayrona was accomplished when vegetative cuttings were taken from the initial selection in January 1990 in a controlled environment in Salinas, Calif., by technicians working under supervision of Cornelis P. VandenBerg.

Horticultural examination of controlled flowerings of successive plantings has shown that the unique combination of characteristics as herein disclosed for Yellow Tayrona are firmly fixed and are retained through successive generations of asexual reproduction.

Yellow Tayrona has not been observed under all possible environmental conditions. The phenotype may vary significantly with variations in environment such as temperature, light intensity and daylength, without, however, any variance in genotype.

The following observations, measurements and comparisons describe plants grown in Salinas, Calif., and in Bogota, Colombia, under greenhouse conditions which approximate those generally used in commercial greenhouse practice. The low night temperature tolerance was determined in repeated flowerings in Bogota, Colombia.

The following traits have been repeatedly observed and are determined to be basic characteristics of Yellow Tayrona, which, in combination, distinguish this Chrysanthemum as a new and distinct cultivar:

1. Flat capitulum form.
2. Decorative capitulum type.
3. Yellow ray floret color, with a fresh green center of the flower.
4. Diameter across face of capitulum of 63 to 73 mm when fully opened, when grown as a single stem spray cut mum.
5. Photoperiodic flowering response to short days when grown in Salinas, Calif., is 50 to 59 days after start of short days. Flowering response in Bogota, Colombia, under temperatures of minimum 7 degrees Celsius night and maximum 29 degrees Celsius day is 63 to 67 days.
6. Plant height is 74 to 79 cm when grown in Salinas with 7 to 10 long days prior to start of short days; height is 99 to 124 cm when grown in Bogota with 14 long days prior to start of short days.
7. Peduncle length of the first lateral at flowering after removing the apical bud without growth regulator applications is 10 to 13 cm when grown in Salinas, and 13 to 18 cm when grown in Bogota. Peduncle length of the fourth lateral at flowering is 13 to 15 cm when grown in Salinas, and 18 to 23 cm when grown in Bogota.
8. Excellent tolerance to minimum low night temperatures of 7° C. for bud initiation and flower development.

The accompanying photographic drawing is a side view of a single stem cut spray mum of Yellow Tayrona, with the colors being as nearly true as possible with illustrations of this type.

Of the commercial cultivars known to the inventor, the most similar in comparison to Yellow Tayrona is the parent cultivar Tayrona. All traits of Yellow Tayrona are similar to those of Tayrona, except for the ray floret color. Yellow Tayrona has a yellow ray floret color, while Tayrona has a white ray floret color. Both Yellow Tayrona and Tayrona have a fresh green center of the flower. In several flowering trials in Salinas and Bogota, slight differences in response time and plant height were noted between Tayrona and Yellow Tayrona. However, these differences were not sufficiently consistent to be considered distinguishing differences.

In the following description color references are made of the Royal Horticultural Society Colour Chart. The color values were determined on plant material grown as a single stem spray cut mum in Salinas, Calif. on Dec. 27, 1991.

Classification:

*Botanical.*—*Dendranthema grandiflora* cv Yellow Tayrona.

*Commercial.*—Flat decorative cut spray mum.

INFLORESCENCE

A. Capitulum:

*Form*—Flat

*Type.*—Decorative.

*Diameter across face.*—63 to 73 mm when fully opened.

B. Corolla of ray florets:

*Color (general tonality from a distance of three meters).*—Yellow, with green center of flower.

*Color (upper surface).*—9A to 9B. Mid center overcast with 144A.

*Color (under surface).*—7A to 7B.

*Shape.*—Outer petals straight, inner petals slightly incurved; cross section concave.

C. Corolla of disc florets:

*Color (mature).*—Closest to 14A.

*Color (immature).*—Closest to 144A.

D. Reproductive organs:

*Androecium.*—Present on disc florets only; scant pollen.

*Gynoecium.*—Present on both ray and disc florets.

PLANT

A. General appearance:

*Height.*—74 to 79 cm when grown in Salinas with 7 to 10 long days prior to start of short days; height is 99 to 124 cm when grown in Bogota with 14 long days prior to start of short days.

B. Foliage:

*Color (upper surface).*—147A.

*Color (under surface).*—147B.

I claim:

1. A new and distinct Chrysanthemum plant named Yellow Tayrona, as described and illustrated.

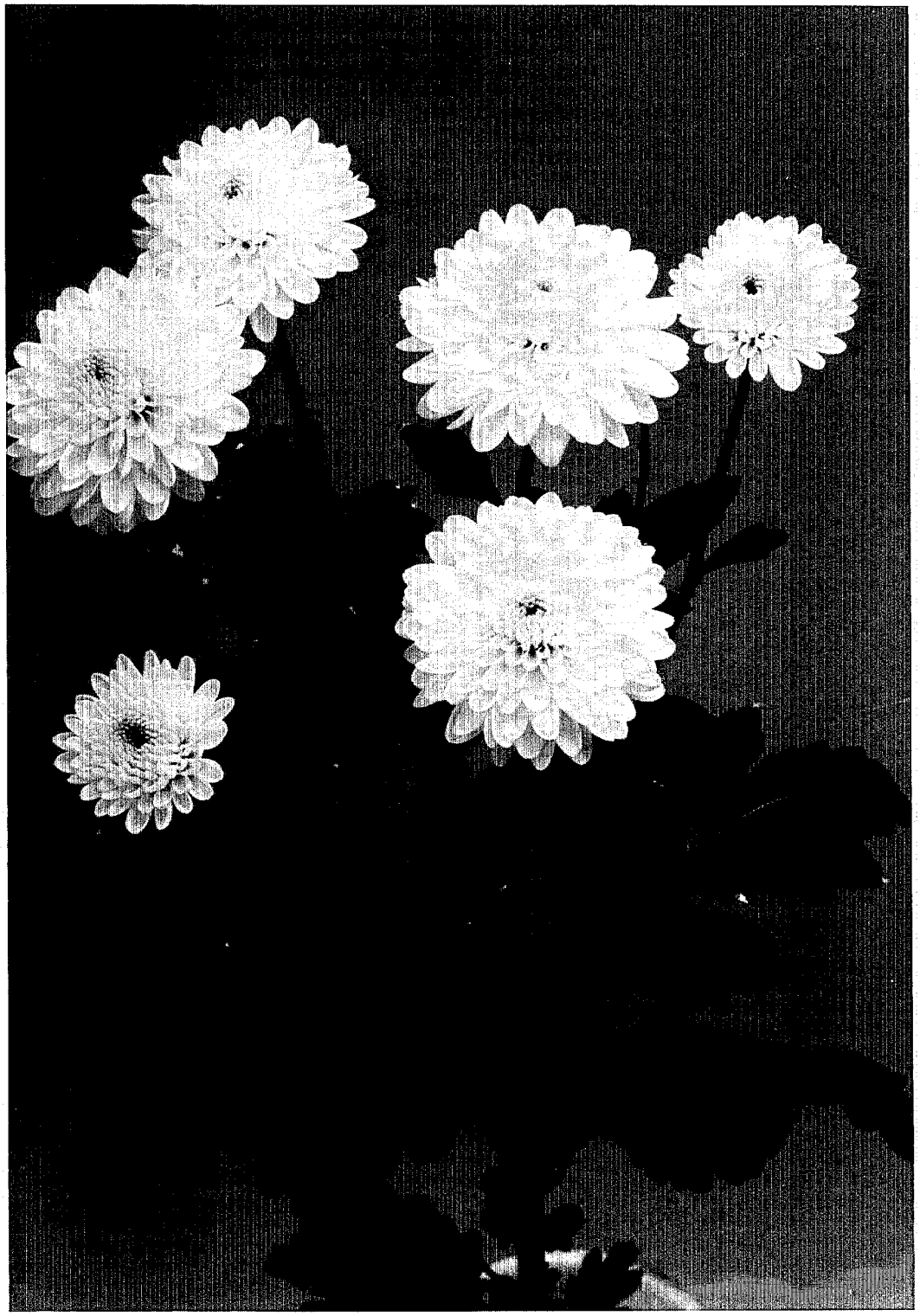

* * * * *